Oct. 9, 1962 D. H. MOREY, JR Plant Pat. 2,182
ROSE PLANT
Filed Nov. 15, 1961
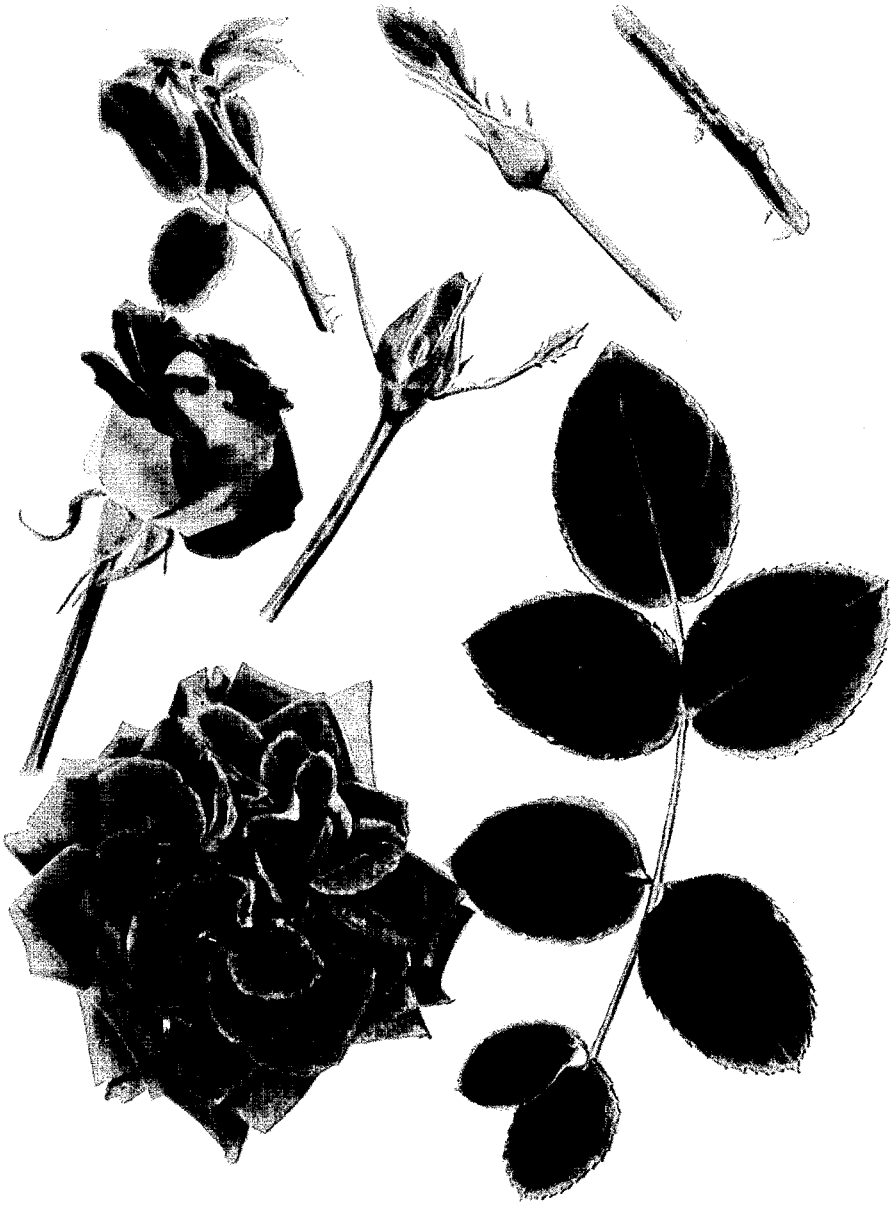
Inventor.
Dennison H. Morey, Jr.
By: Robb & Robb
Attorneys.

United States Patent Office

Plant Pat. 2,182
Patented Oct. 9, 1962

2,182
ROSE PLANT

Dennison H. Morey, Jr., Pleasanton, Calif., assignor to Jackson & Perkins Company, Newark, N.Y., a corporation of New York Filed Nov. 15, 1961, Ser. No. 152,696
1 Claim. (Cl. 47—61)

The present invention relates to a new and distinct variety of rose plant of the hybrid tea class, which was originated by me by crossing the variety "New Yorker" (Plant Patent No. 823) with the variety "Happiness" (Plant Patent No. 911).

The primary objective of this breeding was to produce a new rose variety which bears dark red flowers suitable for garden use and which would not burn under conditions of hot summer sun. This objective was fully achieved, along with other desirable improvements, as evidenced by the following unique combination of characteristics which are outstanding in the new variety and which distinguish it from its parents, as well as from all other varieties of which I am aware:

(1) Good resistance of the flowers to sun burn, with good color retention throughout the hot summer months;

(2) A distinctive and attractive general color tonality of the flowers corresponding to Carmine lightly overcast with Oxblood Red, in both the half open and fully open flowers; and (3) A strong and rich hybrid tea flower scent.

Asexual reproduction of my new variety by budding, as performed at Newark, New York, and also at Pleasanton, California, shows that the aforementioned characteristics and distinctions come true to form and are established and transmitted through succeeding propagations.

The accompanying drawing shows typical specimens of the vegetative growth and flowers of my new variety in different stages of development and as depicted in color as nearly true as it is reasonably possible to make the same in a color illustration of this character.

The following is a detailed description of my new variety, with color terminology in accordance with Ridgway's Color Standards and Nomenclature:

Parentage: Seedling.
*Seed parent.*—"New Yorker."
*Pollen parent.*—"Happiness."

Classification:
*Botanic.*—Hybrid tea.
*Commercial.*—Hybrid tea.

*Flower*

(Observations made from specimens grown outdoors at Newark, New York, in the early morning during the early part of the month of August.)

Blooming habit: Recurrent—continuous.

Bud:
*Size.*—Medium.
*Form.*—Ovoid; is not affected by wet or hot weather.
*Color.*—When sepals first divide—Bordeaux, Plate 12. When petals begin to unfurl—Carmine, Plate 1. When half-blown: inside of petals—Oxblood Red, Plate 1; reverse of petals—Carmine, Plate 1, very lightly overcast with Nopal Red, Plate 1.
*Sepals.*—Branched; curl back when petals begin to unfurl. Color: inside—Light Turtle Green, Plate 32; outside—Light Bice Green, Plate 17.
*Calyx.* — Color — Light Bice Green, Plate 17. Shape — apple. Size — broad. Aspect — smooth. Odor when rubbed—none.
*Peduncle.* — Length — medium. Aspect — smooth. Strength—erect; heavy. Color—Spinach Green, Plate 5.

*Opening.*—Opens up well; is not affected by adverse weather conditions.

Bloom:
*Size.*—Large. Average size when fully expanded—from 5 inches to 5½ inches.
*Borne.*—Singly.
*Stems.*—Long; strong.
*Form (when first open).* — High-centered. Permanence—retains its form to the end.
*Petalage.*—Double (full but open center). Number of petals under normal conditions—from 25 to 30.
*Color.* — Center of flower — Oxblood Red, Plate 1, lightly overcast with Carmine, Plate 1 on the outer edge of the petals. Outer petals — Nopal Red, Plate 1, lightly overcast with Carmine, Plate 1. Base of petals (aiglet)—Amber Yellow, Plate 16. Inside of petals — Carmine, Plate 1, lightly overcast with Oxblood Red, Plate 1. Reverse of petals—Nopal Red, Plate 1, very lightly ocercast with Carmine, Plate 1. General tonality from a distance—Carmine, Plate 1, lightly overcast with Oxblood Red, Plate 1.
*Discoloration.* — General tonality at end of first day—Oxblood Red, Plate 1, lightly overcast with Carmine, Plate 1. Second day—Carmine, Plate 1, lightly overcast with Oxblood Red, Plate 1. Third day—Nopal Red, Plate 1, very lightly overcast with Carmine, Plate 1.

Petals:
*Texture.*—Leathery; is not affected by wet or hot weather.
*Appearance.*—Inside—velvety. Outside—satiny.
*Form.*—Oval.
*Arrangement.*—Imbricated (regularly arranged shingle-like).
*Petaloids in center.*—Few; large.
*Persistence.*—Drop off cleanly.
*Fragrance.*—Strong. Nature—rich tea.
*Lasting quality.*—On plant—long. As cut flower—long.

*Genital Organs*

Stamens, anthers: Medium size; many; regularly arranged around styles. Color—Orange-Cinnamon, Plate 29.
Stamens, filaments (threads): Medium length. Color—Eugenia Red, Plate 13.
Pollen: Color—Pale Cinnamon-Pink, Plate 29.
Styles: Bunched; uneven length; medium length; thin.
Ovaries: All enclosed in calyx.
Hips: None.
Seeds: None.

*Plant*

Form: Bush.
Growth: Vigorous; upright.
Foliage: Compound of 3–7 leaflets.
*Size.*—Large.
*Quantity.*—Abundant.
*Color.*—New foliage: upper side—Bice Green, Plate 17, with center rib Acajou Red, Plate 13; under side — Oil Green, Plate 5, lightly overcast with Pompeian Red, Plate 13. Old foliage: upper side—Varley's Green, Plate 18; under side—Light Cress Green, Plate 31.
*Shape.*—Oval.
*Texture.* — Upper side — leathery. Under side — smooth.
*Ribs and veins.*—Ordinary.
*Edge.*—Serrated (saw-toothed).
*Serration.*—Both double and single; small.
*Leaf stem.*—Color—Spinach Green, Plate 5. Under side—smooth.

*Stipules.*—Medium length; smooth.

Wood:

*New wood.*—Color—Grass Green, Plate 6. Bark—smooth.

*Old wood.*—Color—Forest Green, Plate 17. Bark—smooth.

Thorns:

*Thorns.*—Quantity: on main stalks from base—ordinary; on laterals from stalk—ordinary. Form—narrow base; medium length; some straight and some hooked downward. Color (when young)—Eugenia Red, Plate 13. Position—irregular.

*Prickles.*—Quantity: on main stalks—none; on laterals—none.

*Short needles.*—Quantity: on main stalks—none; on laterals—none.

I claim:

A new and distinct variety of rose plant of the hybrid tea class, substantially as herein shown and described, characterized particularly as to novelty by the unique combination of good resistance of the flowers to sun burn and good retention of the flower color throughout the hot summer months, a distinctive and attractive general color tonality of the flowers corresponding to Carmine lightly overcast with Oxblood Red, in both the half open and fully open flower stages, and a strong and rich tea fragrance of the flowers.

No references cited.